United States Patent [19]

McGarrity et al.

[11] Patent Number: 4,855,227

[45] Date of Patent: Aug. 8, 1989

[54] RAPID DETECTION OF MYCOPLASMAS

[75] Inventors: Gerard J. McGarrity, Wenonah; Hitoshi Kotani, Cherry Hill, both of N.J.

[73] Assignee: Institute for Medical Research, Camden, N.J.

[21] Appl. No.: 742,469

[22] Filed: Jun. 7, 1985

[51] Int. Cl.$^4$ .................. G01N 33/543; G01N 33/569
[52] U.S. Cl. .......................................... 435/7; 435/21; 435/28; 435/34; 435/870; 436/530; 436/531; 436/547; 436/804; 436/805; 436/811
[58] Field of Search ...................... 435/7, 21, 28, 870, 435/34; 436/530, 531, 804, 805, 811, 547

[56] References Cited

U.S. PATENT DOCUMENTS 3,485,721 12/1969 Woodhour .......................... 435/870
4,666,851 5/1987 Lee ......................................... 435/7

FOREIGN PATENT DOCUMENTS 2095258 9/1982 United Kingdom .

OTHER PUBLICATIONS

Gershoni, Analytical Biochemistry 131, 1–15 (1983).
Baseman, Infection & Immunity 43(3), pp. 1103–1105 (1984).
Busolo, J Clinical Microbiology 18(2), pp. 432–435 (1983).
Yolken, Reviews of Infectious Diseases 4(1), pp. 35–42 (1982).
Salamova, Biological Abstracts, vol. 81 #33470 (1985).
Hsu, "Immunogold for Detection of Antigen on Nitrocellulose Paper", Analytical Biochemistry, 142, 221–225 (1984).
Hawkes et al., "A Dot-Immonobinding Assay for Monoclonal and Other Antibodies", Analytical Biochemistry 119, 142–147 (1982).
Dussaix et al., "Comparison of Enzyme-Linked Immunosorbent Assay (ELISA) and Complement Fixation Test for Detection of *Mycoplasma pneumoniae* Antibodies", J. Clin. Pathol. 36, 228–232 (1983).
Monroe, "The Solid-Phase Enzyme-Linked Immonospot Assay: Current and Potential Applications", Biotechniques, 222–228, (May/Jun. 1985).
Wreghitt, et al., Journal of Hygiene (1985), vol. 94, pp. 217–227.
Raisanen, et al., Journal of Clinical Pathology (1984), vol. 37, pp. 1129–1133.
Brunner, et al., Medical Microbiology and Immunology (1978), vol. 165, pp. 29–41.
Nature, (1983) vol. 306, No. 5942.

Primary Examiner—Robert J. Warden
Assistant Examiner—Robert Benson
Attorney, Agent, or Firm—Banner, Birch, McKie & Beckett

[57] ABSTRACT

A clinical diagnostic method capable of rapidly detecting the presence of *Mycoplasma pneumoniae* in infected humans is taught. The method allows a proper course of therapy to be chosen within one day of presentation of the patient.

25 Claims, No Drawings

RAPID DETECTION OF MYCOPLASMAS

BACKGROUND OF THE INVENTION

This invention relates to the detection of *Mycoplasma pneumoniae* in humans.

Mycoplasma are distinct from bacteria; they are smaller, completely lack a cell wall, and contain only about 1/6th the amount of DNA that bacteria have. Like bacteria, many mycoplasma can cause diseases of humans, other animals and plants. However, the diseases are often difficult to treat with antibacterial agents due to the inherent resistance of mycoplasma to antibiotics which affect cell walls such as the penicillins. In addition, the detection of mycoplasma in diseased hosts by standard microbiological techniques is often difficult because many types cannot be grown in culture.

Many human diseases are associated with mycoplasmal infection, including: primary atypical pneumonia, non-gonococcal urethritis, chorioamnionitis, low birth weight, pelvic inflammatory disease, postabortal fever, postpartum fever and pyelonephritis. In some cases a causal relationship has been proven between mycoplasma and the disease.

It has been said that *Mycoplasma pneumoniae* causes from 5% to 20% of all human pneumonias. In closed populations, such as college students and military personnel, the rate is even higher, about 20% to 45%. *M. pneumoniae* cannot be isolated from the blood of infected patients, but can be isolated from the nose, throat, sputum and trachea. However, only about $10^3$ to about $10^5$ colony forming units per swab of *M. pneumoniae* are found in such specimens and they are difficult to culture and slow growing.

*M. pneumoniae* grow best anaerobically on an extremely complex medium, containing enriched peptone, yeast extract and horse serum. These are not the standard conditions used in a clinical microbiology laboratory, so *M. pneumoniae* often goes undetected. Furthermore, even if optimized conditions are used, the organisms still require a 10 to 14 day incubation period. These factors make standard serological and sugar fermentation tests impractical as tools for clinical diagnosis.

The routine antibiotic therapy for human pneumonia involves penicillin or ampicillin, which are ineffective in killing mycoplasma; however, there are effective antibiotics, such as erthyromycin, which can control mycoplasma infections. Therefore, there is a need for a clinical diagnostic method capable of rapidly detecting *Mycoplasma pneumoniae* in infected humans so that a proper course of antibiotic therapy may be chosen promptly.

SUMMARY OF THE INVENTION

It is an object of the present invention to provide method for detecting mycoplasma.

It is an object of the present invention to provide a rapid method for detection of mycoplasmal infections in humans.

In accordance with this invention there is provided a method for rapid detection of *Mycoplasma pneumoniae* in human secretions and specimens comprising: applying said secretion or a suspension of the specimen to a solid support and allowing it to dry, contacting the solid support with a primary antibody raised against *Mycoplasma pneumoniae,* contacting the solid support with a secondary antibody raised against immunoglobulin of the species of the primary antibody, said secondary antibody bearing a means of detection. Also provided is an alternate method in which the primary antibody is applied first to the solid support.

DETAILED DESCRIPTION OF THE INVENTION

A means of diagnosis of *M. pneumoniae* infections in humans has been found which is sensitive, specific, and rapid. Sensitivity is crucial to the finding because there are only small numbers of the causative organisms present in mucosal secretions and infected tissues. Typically between $5 \times 10^3$ and $1 \times 10^5$ colony forming units are present in swabbings of such areas. The present invention can detect down to levels of about $1.8 \times 10^4$ colony forming units.

Specificity of the present method is important because *Mycoplasma pneumoniae* are typically isolated together with two other species of mycoplasma, *M. orale* and *M. salivarium.* These two species are not pathogenic and are found in the mouths of many healthy people. Therefore, it is important that the diagnostic method distinguish between the pathogenic *M. pneumoniae* and the nonpathogenic mycoplasms. The presence of either or both nonpathogenic species in a sample does not cause the present method to yield positive results for *M. pneumoniae* when no *M. pneumoniae* are present.

The present invention is rapid enough to be preformed within about 4 hours. Thus, it can be useful in selecting an appropriate course of antibiotic therapy. Alternative methods of identification of *Mycoplasma pneumoniae* require growth of the microorganisms for a minimum of 10 to 14 days. This can either delay therapy for that period of time, or delay appropriate antibiotic administration.

Samples which can be tested by the present method can be derived from saliva, sputum, throat or nasopharyngeal swabs, tracheal aspirates and biopsy specimens. Organisms collected from swabs can be resuspended by immersion in a suitable buffered solution, such as TBS (50 mM tris-HCl, 200 mM NaCl, pH 7.4). For example, a volume of about 1.5 mls is sufficient for immersion of a swab. The suspension can be concentrated by centrifugation at $15,000 \times g$ for about 10 minutes followed by resuspension of the pellet in about 15 to 500 ul. A choice of other buffered solutions and other concentration techniques are easily within the skill of the art.

Samples which are already supsensions do not need to be concentrated further. Biopsy specimens should be homogenized, by any of the techniques well known in the art, such as using a Potter-Elvejhem homogenizer or a Waring blender. The sample should be homogenized in a minimum amount of buffer to maintain sufficient concentrations of mycoplasma. For example, 1 gram of biopsy tissue should be homogenized in about 2 ml of buffer. It is to be noted that blood typically does not contain sufficient numbers of mycoplasma to be detectable.

The solid support employed in the practice of this invention is one that binds to proteins or other antigenic components of the mycoplasma cells. Paper which is preferably used as a solid support in the method of the present invention is desirably made of nitrocellulose. However, other solid supports can be used such as diazobenzyloxymethyl (DBM) modified cellulose paper and nylon-based membranes, such as Zetabind ™. The choice of still other solid supports is within the skill of the art. The solid support is typically pre-washed in distilled water. Such washing and all subsequent washing steps during the assay can readily be accomplished by mild agitation of the solid support in a small reservoir of the liquid. This and all steps of the assay procedure can be performed at room temperature. After one washing the paper is allowed to dry.

Samples prepared as described above are applied to the solid support in about 1 to 10 ul volumes. The location of particular samples can be marked beforehand with a pencil or waterproof ink, or the solid support may be cut into small (about 2.5 cm) squares and kept in individual petri plates. Other means of marking will readily occur to one. The applied liquid is allowed to dry. If higher concentrations of sample are desired, multiple applications of the sample can be made to the same area of paper, allowing the liquid to evaporate between applications.

If it is desired to kill the mycoplasma to reduce the risk of infection to the clinician, the paper can be washed in a solution of 10% formalin for about 10 minutes followed by washing with TBS for about 5 minutes to remove the formalin. Other killing treatments can be employed without adversely affecting the assay such as detergent or heat. If desired, the mycoplasma can also be killed before it is applied to the substrate.

If the ultimate means of visual detection of results of the assay are to involve the enzyme peroxidase, it may be advantageous to eliminate any contaminating peroxidases which may be present on the solid support. To do so, the solid support can be washed in a 0.3% solution of hydrogen peroxide in TBS for about 10 minutes. The solid support should then be washed with TBS for about 5 minutes.

A blocking solution (which consists of a concentrated proteinaceous solution) is used to fill all protein binding sites on the solid support not already filled by the sample. Such blocking solutions are used to preclude the binding of antibodies directly to the solid support. A typical blocking solution contains about 10% horse serum and 0.02% Tween 20. Alternatively, bovine serum albumin or any protein which will not react with the antibodies to be employed in the assay can be used. The solid support is washed in the blocking solution for about 30 minutes.

The primary antibody which is applied to the solid support may be either polyclonal or monoclonal in origin. It may be derived from mouse, rat, horse, cow, goat, rabbit or any other suitable animal species. The primary antibody should be reactive with *M. pneumoniae*, preferably with a surface antigen of *M. pneumoniae*. It should not cross react with other species of mycoplasma. Such antibodies can be raised by inoculation of an animal with *M. pneumoniae* or antigen preparations derived from *M. pneumoniae*. After a suitable period the animals are bled and the serum containing the appropriate antibodies is collected. Such techniques are well known in the art.

Monoclonal antibodies can be obtained by fusing splenocytes from inoculated animals with myeloma cells, preferably of the same species. Successfully fused cells are selected and isolated and screened for the production of antibodies which react with *M. pneumoniae*. Such antibodies are secreted into the growth medium. Techniques for raising monoclonal antibodies are well known in the art. Suitable antibodies raised against *M. pneumoniae* are available commercially from Bethesda Research Laboratories, Gaithersburg, MD.

The primary antibody is incubated with the solid support containing sample and blocking proteins. The incubation is carried out for about 30 minutes to about 120 minutes in a minimum volume, for example, 10 microliters for a 2.5 cm square.

If the antibodies are to be diluted before use, they are diluted into blocking solution, described above. A suitable dilution factor is often found to be between about $10^{-2}$ and $10^{-3}$. Optimum dilution factors can be determined for a particular antibody preparation by routine testing. It is important to optimize this factor to minimize nonspecific binding of antibody to the solid support or applied proteins. The solid support is then washed to remove unbound primary antibody with, for example, three washings, with TBS.

In an alternative embodiment of the invention the primary antibody is applied first to the solid support and allowed to dry. The solid support is then contacted with blocking solution before application of the test sample. All subsequent steps are performed identically in the two embodiments. Thus, either the test sample or the primary antibody may be used to anchor the reaction to the solid support.

The secondary antibody is derived from a different species of animal than that of the primary antibody. The secondary antibody is raised against immunoglobulin of the species of the primary antibody. So that if the primary antibody is a rabbit anti-mycoplasma antibody, the secondary antibody could be a goat anti-rabbit immunoglobulin antibody. Obviously, other combinations can also be employed.

In addition, the secondary antibody bears a means of detection. Such means is often an enzyme which is conjugated to the antibody. When incubated with appropriate substrates a colored product is formed at the area of the solid support where the enzyme is bound. Thus, a colored reaction product indicates that the original sample applied to the solid support in that position contained antigen recognized by the primary antibody. The secondary antibody is merely an amplification system, allowing more of the means of detection to be clustered at the site of the original antigen.

Examples of enzymes which produce a colored product and can be conjugated to the secondary antibody are alkaline phosphatase and horseradish peroxidase. Alternatively, the secondary antibody may be labeled with gold which is directly visible as a pink color without further treatment. Still other means of detection involves a secondary antibody which is labeled with a radioactive compound. If the proper antigen is present there would result a concentration of radioactivity at the spot where the specimen was applied. Radioactivity can be detected by autoradiography, liquid scintillation counting, a geiger counter, or any other means known in the art.

If a developing solution is necessary to provide substrates to the antibody-linked enzyme, it an be supplied in a wash of the solid support. In the case of horseradish peroxidase, a suitable solution contains 4-chloro-naphthol (0.5 mg/ml) and hydrogen peroxide (0.01%). Typically the color will develop within about 1 to 5 minutes. After the color develops the solid support is rinsed with distilled water, air dried, and stored in the dark. In the case of alkaline phosphatase, a suitable developing solution contains p-nitrophenylphosphate. When the phosphate group is cleaved from the substrate a yellow-colored product is formed. For other enzymes the substrates required will vary as may the time required to develop the color. These enzyme systems are well known in the art.

The following examples are included for exemplification only and are not intended to limit the scope of the invention.

EXAMPLE 1

This example shows that the assay of the present invention is specific and sensitive.

Mycoplasma and Media

Ten mycoplasma and one acholeplasma species were used. All strains except those mentioned below were obtained from the American Type Culture Collection, Rockville, Md. *M. fermentans* strain HK was an isolate from cell cultures in our laboratory, and has been triply cloned; *M. gallisepticum* strain PG 31 and *M. pulmonis* PG 34 were kindly provided from J.G. Tully of the National Institute of Allergy and Infectious Disease, Bethesda, Maryland. The strains were cultured in mycoplasma broth as described previously (G. McGarrity, "Detection of Mycoplasmal Infection of Cell Cultures," in *Advances in Cell Cultures*, K. Maramorosch, editor, Academic Press, N.Y., 1982, pp. 99–131.

All strains were grown at 37° C. The number of colony forming units per ml of mycoplasma was determined by inoculation onto complex agar medium of serial dilutions of a sample.

Mycoplasma were also grown in cell culture on 3T6 mouse embryo fibroblast cells. 3T6 cells were grown in McCoy's medium and 10% fetal bovine serum. To initiate infection, approximately $10^5$ colony forming units of the respective mycoplasma were inoculated into 3T6 cells. The flasks were incubated at 37° C. in 5% carbon dioxide in air for 4 to 5 days. The supernatants of these infected cultures were used as antigens.

Polyclonal and Monoclonal Antibodies

Polyclonal antisera against all strains were made using the method described by Senterfit (in *Methods in Mycoplasmology*, volume 1, Razin, S. and Tully, J.G., editors, Academic Press, N.Y., 1983, pp. 401–404). Monoclonal antibodies against *M. hyorhinis, M. arginini, M. salivarium, M. orale* and *A. laidlawii* obtained from Bethesday Research Laboratories were also used. In general an antibody concentration of about a 1:1000–1:5000 dilution was found to be optimal, virtually eliminating nonspecific binding.

Both supernatants of infected 3T6 cells and broth cultures of mycoplasma were applied onto nitrocellulose paper. The nitrocellulose paper was obtained from the Millipore Corporation, and was cut into squares of approximately 2.5 cm. The paper was placed in plastic petri dishes of approximately 6 cm diameter, and washed in distilled water for 5 minutes and air dried before being used.

The assay was performed at room temperature with mild agitation. Ten ul of each of the test specimens, supernatant from cell cultures, and broth cultures were applied to each square. Mycoplasmas were killed by applying a 10% buffered formalin solution for 10 minutes. The nitrocellulose was treated to inactivate any exogenous peroxidase by addition of 0.3% hydrogen peroxide in TBS for 10 minutes and was subsequently washed with TBS for 5 minutes.

A blocking solution of 10% horse serum and 0.2% Tween 20 was added to the paper for 30 minutes. The appropriate polyclonal or monoclonal antibody in blocking solution was then applied to the paper in a volume of 1 ml. These antibodies were raised against individual mycoplasmal species. The paper was incubated at room temperature for 30 minutes with an antibody and washed three times with TBS for 10 minutes each wash.

As a secondary antibody, peroxidase labeled anti-rabbit IgG or anti-mouse IgG obtained from Miles Laboratories, in blocking solution was applied for 30 minutes to the solid support, followed by three washings with TBS.

Developing solution consisting of 3 mg of 4-chloro-1-naphthol in 1 ml of methanol, 5 mls of TBS and 0.01% hydrogen peroxide, was added to the solid support. If a positive reaction occurred, a purple color appeared in one to five minutes. After the reaction was completed, before background coloration occurred, the paper was washed with distilled water and allowed to dry. Both supernatants of 3T6 cells which have been infected with mycoplasma and broth culture of mycoplasma gave specific purple spots (positive reaction) using homologous polyclonal antibody, without cross reaction. Some slight background coloration of the paper appeared in a few cases. When monoclonal antibodies against *A. laidlawii, M. hyorhinis, M. arginini, M. salivarium* and *M. orale* were used as primary antibodies, clear reactions were obtained without any nonspecific reactions.

The sensitivity of this method was determined by performing ten-fold serial dilutions of broth cultures of each species and applying them to the same nitrocellulose paper. The end point of positive detection was determined. The results of these determinations are shown in Table 1, below.

TABLE 1

Sensitivity and Specificity of Immunobinding Assay on 3T6 Cell and Mycoplasma Broth Inoculated Mycoplasma

| Organism | Strain | Culture[a] 3T6 cells | Mycoplasma Broth | Sensitivity (CFU/ml) |
| --- | --- | --- | --- | --- |
| A. laidlawii | JS | + | + | $1.1 \times 10^4$ |
| M. hyorhinis | GDL | + | + | ND[b] |
| M. hominis | PG 21 | + | + | $2.5 \times 10^4$ |
| M. arginini | VA | + | + | $9.3 \times 10^3$ |
| M. salivarium | VV | + | + | $7.5 \times 10^4$ |
| M. orale | MG | + | + | $2.6 \times 10^4$ |
| M. pirum | 70-159 | + | + | ND |
| M. fermentans | HK | + | + | $1.5 \times 10^4$ |
| M. pneumoniae | FH | ND | + | $2.2 \times 10^4$ |
| M. pneumoniae | M129-B16 | ND | + | $1.8 \times 10^4$ |
| M. pulmonis | PG 34 | ND | + | ND |
| M. gallisepticum | PG 31 | ND | + | ND |

[a]No crossreaction occurred among these strains using polyclonal antibodies against all species and monoclonal antibodies against *A. laidlawii, M. hyorhinis, M. arginini, M. salivarium* and *M. orale*.
[b]Not done.

EXAMPLE 2

This example demonstrates that the present invention can detect the presence of mycoplasma and distinguish one species from another in specimens derived from human mouths.

Oral swab samples were taken from eight apparently healthy persons and six persons with respiratory symptoms. Both microbiological assay and the immunobinding assay of the present invention were performed on these specimens, as described in Example 1. There was a 100% correlation between the two assay methods. As can be seen in Table 2 patients 3, 4, 11, and 14 were positive for the nonpathogenic mycoplasma and yet the immunobinding assay was capable of distinguishing these organisms from *M. pneumoniae*.

TABLE 2

Comparison of Microbiological Culture and Immunobinding Assay on Human Oral Specimens

| Sample[a] | M. orale MA[b] | M. orale IBA[c] | M. salivarium MA | M. salivarium IBA | M. pneumoniae MA | M. pneumoniae IBA |
|---|---|---|---|---|---|---|
| 1 | − | − | − | − | − | − |
| 2 | − | − | − | − | − | − |
| 3 | + | + | + | + | − | − |
| 4 | + | + | + | + | − | − |
| 5 | + | + | + | + | + | + |
| 6 | − | − | − | − | − | − |
| 7 | − | − | − | − | − | − |
| 8 | − | − | − | − | − | − |
| 9 | + | + | + | + | + | + |
| 10 | + | + | + | + | + | + |
| 11 | − | − | + | + | − | − |
| 12 | − | − | − | − | − | − |
| 13 | − | − | − | − | − | − |
| 14 | − | − | + | + | + | + |

[a]Samples 1–8: apparently healthy people
Samples 9–13: patients with respiratory symptoms
[b]Microbiological Assay
[c]Immunobinding Assay Since modifications of this invention will be apparent to those skilled in the art, it is intended that the scope of the invention be limited only by the scope of the appended claims.

We claim:

1. A diagnostic method for rapid detection of Mycoplasma pneumoniae in human secretions and specimens comprising:
   applying said secretion or a suspension of the specimen comprising $10^5$ or less colony forming units of *M. pneumoniae* to a solid support comprising a nitrocellulose paper and allowing it to dry; then
   filling unoccupied protein binding sites of the solid support by contacting with a blocking solution comprising horse serum and polyoxyethylene sorbitan monolaurate; then
   contacting the solid support with a primary antibody raised in a first vertebrate species against *Mycoplasma pneumoniae*; then
   contacting the solid support with a secondary antibody raised against immunoglobulin of the species of the primary antibody, said secondary antibody bearing a means of detection; then
   detecting the presence of said secondary antibody bound to said solid support utilizing said means of detection, and relating said bound secondary antibody to the presence of *Mycoplasma pneumoniae*.

2. The method of claim 1 wherein the means of detection is an enzyme conjugated to the secondary antibody, wherein the solid support is further contacted with a developing solution containing chromogenic substrates for the enzyme.

3. The method of claim 2 wherein the enzyme is horseradish peroxidase and the developing solution consists essentially of 4-chloro-1-naphthol and hydrogen peroxide.

4. The method of claim 2 wherein the enzyme is alkaline phosphatase and the developing solution contains p-nitrophenylphosphate.

5. The method of claim 1 wherein the secondary antibody is labeled with gold.

6. The method of claim 1 wherein the secondary antibody is labeled with a radioactive compound, and the means of detection is autoradiography.

7. The method of claim 1 wherein the secondary antibody is labeled with a radioactive compound and the means of detection is by liquid scintillation counting.

8. The method of claim 1 wherein the primary antibody is a polyclonal antibody.

9. The method of claim 1 wherein the human secretion is selected from the group consisting of sputum, saliva, and tracheal aspirates.

10. The method of claim 1 wherein the human specimens is selected from the group consisting of throat swabs, nasopharyngeal swabs and biopsy tissues.

11. The method of claim 1 wherein after the secretion or suspension has been applied to the solid support, said secretion or suspension of the specimen is treated with formalin to kill mycoplasma.

12. A diagnostic method for rapid detection of Mycoplasma pneumoniae in human secretions and specimens comprising:
   contacting a solid support comprising a nitrocellulose paper with a primary antibody raised in a first vertebrate species against *Mycoplasma pneumoniae* and allowing it to dry; then
   filling unoccupied protein binding sites of the solid support by contacting with a blocking solution comprising horse serum and polyoxyethylene sorbitan monolaurate; then
   applying the human secretion or a suspension of the specimen comprising $10^5$ or less colony forming units of *M. pneumoniae* to the solid support; then
   contacting the solid support with a primary antibody raised in a second vertebrate species against *Mycoplasma pneumoniae*; then
   contacting the solid support with a secondary antibody raised against immunoglobulin of the second vertebrate species, said secondary antibody bearing a means of detection; then
   detecting the presence of said secondary antibody bound to said solid support utilizing said means of detection, and relating said bound secondary antibody to the presence of *Mycoplasma pneumoniae*.

13. The method of claim 12 wherein the means of detection is an enzyme conjugated to the secondary antibody, wherein the solid support is further contacted with a developing solution containing chromogenic substrates for the enzyme.

14. The method of claim 13 wherein the enzyme is horseradish peroxidase and the developing solution consists essentially of 4-chloro-1-naphthol and hydrogen peroxide.

15. The method of claim 13 wherein the enzyme is alkaline phosphatase and the developing solution contains p-nitrophenylphosphate.

16. The method of claim 12 wherein the secondary antibody is labeled with gold.

17. The method of claim 12 wherein the secondary antibody is labeled with a radioactive compound, and the means of detection is autoradiography.

18. The method of claim 12 wherein the secondary antibody is labeled with a radioactive compound and the means of detection is by liquid scintillation counting.

19. The method of claim 12 wherein the primary antibodies are monoclonal antibodies.

20. The method of claim 12 wherein the primary antibodies are polyclonal antibodies.

21. The method of claim 12 wherein the human secretion is selected from the group consisting of sputum, saliva, and tracheal aspirates.

22. The method of claim 12 wherein the human specimens is selected from the group consisting of throat swabs, nasopharyngeal swabs and biopsy tissues.

23. The method of claim 12 wherein after the secretion or suspension has been applied to the solid support, said secretion or suspension of the specimen is treated with formalin to kill mycoplasma.

24. A diagnostic method for rapid detection of Mycoplasma pneumoniae in human secretions and specimens comprising:
   applying the human secretion or a suspension of the human specimen comprising $10^5$ or less colony forming units of *M. pneumoniae* to a nitrocellulose paper and allowing it to dry; then
   filling unoccupied protein binding sites of the nitrocellulose paper by contacting with a blocking solution comprising horse serum and polyoxyethylene sorbitan monolaurate; then
   contacting the solid support with a primary antibody raised against *Mycoplasma pneumoniae*, said primary antibody being a monoclonal antibody; then
   contacting the solid support with a secondary antibody raised against immunoglobulin of the species of the primary antibody, said secondary antibody bearing a means of detection; then
   detecting the presence of said secondary antibody bound to said solid support utilizing said means of detection, and relating said bound secondary antibody to the presence of *Mycoplasma pneumoniae*.

25. The method of claim 24 wherein after the secretion or suspension has been applied to the nitrocellulose paper, said secretion or suspension of the specimen is treated with formalin to kill mycoplasma.

* * * * *